United States Patent
Patel et al.

(10) Patent No.: US 11,751,790 B1
(45) Date of Patent: Sep. 12, 2023

(54) PROTECTIVE CIRCUITRY FOR EXTERNAL SENSING APPLICATIONS

(71) Applicant: Apple Inc., Cupertino, CA (US)

(72) Inventors: Priyank Dineshbhai Patel, San Jose, CA (US); Nilay D. Jani, San Jose, CA (US)

(73) Assignee: Apple Inc., Cupertino, CA (US)

( * ) Notice: Subject to any disclaimer, the term of this patent is extended or adjusted under 35 U.S.C. 154(b) by 931 days.

(21) Appl. No.: 16/551,704

(22) Filed: Aug. 26, 2019

Related U.S. Application Data

(60) Provisional application No. 62/844,106, filed on May 6, 2019.

(51) Int. Cl.
| | |
|---|---|
| *A61B 5/276* | (2021.01) |
| *H03K 17/687* | (2006.01) |
| *A61B 5/00* | (2006.01) |
| *A61B 5/339* | (2021.01) |

(52) U.S. Cl.
CPC ............. *A61B 5/276* (2021.01); *A61B 5/339* (2021.01); *A61B 5/681* (2013.01); *A61B 5/6826* (2013.01); *A61B 5/7221* (2013.01); *H03K 17/687* (2013.01); *A61B 2562/0209* (2013.01)

(58) Field of Classification Search
CPC ....... A61B 5/276; A61B 5/681; A61B 5/7221; H03K 17/687; A61B 2562/0209
See application file for complete search history.

(56) References Cited

U.S. PATENT DOCUMENTS

| | | | |
|---|---|---|---|
| 5,483,261 A | 1/1996 | Yasutake | |
| 5,488,204 A | 1/1996 | Mead et al. | |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |

(Continued)

FOREIGN PATENT DOCUMENTS

| | | |
|---|---|---|
| JP | 2000-163031 A | 6/2000 |
| JP | 2002-342033 A | 11/2002 |

OTHER PUBLICATIONS

Ha et al., "Integrated Circuits and Electrode Interfaces for Noninvasive Physiological Monitoring", IEEE Transactions on Biomedical Engineering, Vol. 61, No. 5, May 2014, pp. 1522-1537.

Harrison et al., "A Low-Power Low-Noise CMOS Amplifier for Neural Recording Applications", IEEE Journal of Solid-State Circuits, Vol. 38, No. 6, Jun. 2003, pp. 958-965.

Lee et al., "A Multi-Touch Three Dimensional Touch-Sensitive Tablet", CHI'85 Proceedings, Apr. 1985, pp. 21-25.

(Continued)

*Primary Examiner* — Paula J Stice
(74) *Attorney, Agent, or Firm* — Kubota & Basol LLP

(57) ABSTRACT

Galvanic corrosion of an external electrode of a physiological signal sensor (e.g., ECG sensor) can be reduced. In some examples, protective circuitry, such as a switching circuit, can be used to reduce galvanic corrosion. In a first mode of operation (e.g., corresponding to measurement by the physiological signal sensor), the switching circuit can provide a low-impedance path (e.g., from an external electrode to ground). In a second mode of operation (e.g., corresponding to non-measurement by the physiological sensing system), the switching circuit can provide a high-impedance path to reduce leakage currents (e.g., between the external electrode and ground), and thereby reduce galvanic corrosion.

17 Claims, 11 Drawing Sheets

(56) References Cited

U.S. PATENT DOCUMENTS

| | | | |
|---|---|---|---|
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 8,479,122 | B2 | 7/2013 | Hotelling et al. |
| 2006/0197753 | A1 | 9/2006 | Hotelling |
| 2013/0079659 | A1* | 3/2013 | Akhadov et al. ...... A61B 5/369 600/544 |
| 2016/0066853 | A1 | 3/2016 | Cheng et al. |
| 2017/0238865 | A1 | 8/2017 | Youm et al. |
| 2019/0001131 | A1* | 1/2019 | Ziv .................. A61N 1/36592 |

OTHER PUBLICATIONS

Rubine, Dean H., "Combining Gestures and Direct Manipulation", CHI'92, May 3-7, 1992, pp. 659-660.

Rubine, Dean H., "The Automatic Recognition of Gestures", CMU-CS-91-202, Submitted in Partial Fulfillment of the Requirements for the Degree of Doctor of Philosophy in Computer Science at Carnegie Mellon University, Dec. 1991, 285 pages.

Westerman, Wayne, "Hand Tracking, Finger Identification, and Chordic Manipulation on a Multi-Touch Surface", A Dissertation Submitted to the Faculty of the University of Delaware in Partial Fulfillment of the Requirements for the Degree of Doctor of Philosophy in Electrical Engineering, 1999, 363 pages.

\* cited by examiner

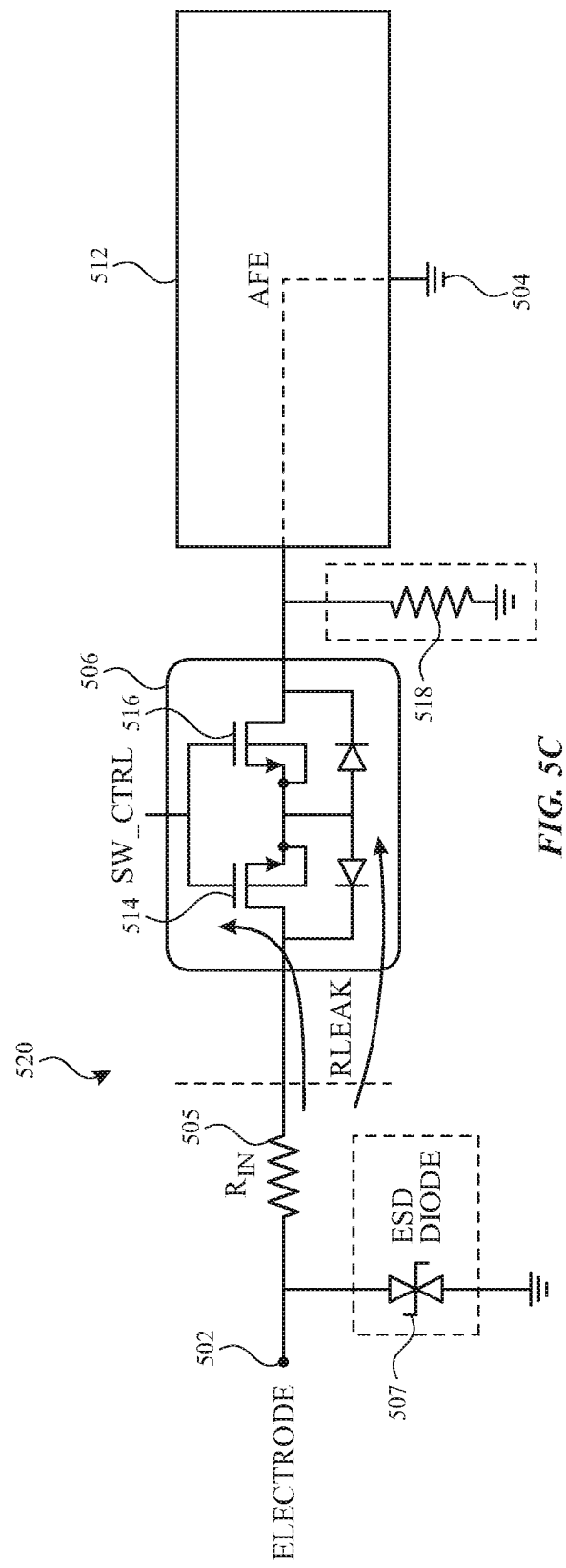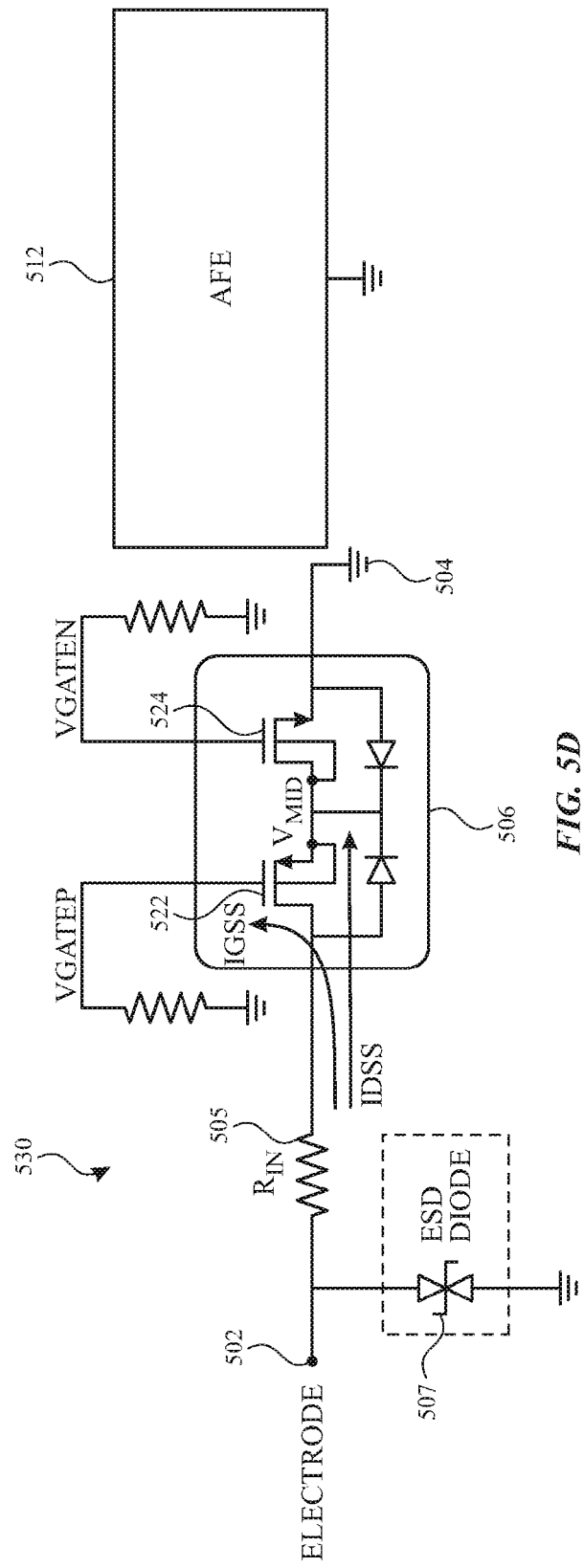
FIG. 5C
FIG. 5D

US 11,751,790 B1

PROTECTIVE CIRCUITRY FOR EXTERNAL SENSING APPLICATIONS

CROSS REFERENCE TO RELATED APPLICATIONS

This application claims the benefit under 35 U.S.C. 119(e) of U.S. Provisional Pat. Application No. 62/844,106, filed May 6, 2019, the content of which is incorporated herein by reference in its entirety for all purposes.

FIELD

This relates generally to protective circuitry for external sensing applications, and more particularly, to protective circuitry for reducing galvanic corrosion of an electrode used in external sensing applications.

BACKGROUND

Electrocardiogram (ECG) waveforms can be generated based on the electrical activity of the heart during each heartbeat. The waveforms can be recorded from multiple electrical leads attached to various areas of a patient. For example, a 12-lead ECG system with a group of ten measurement electrodes that can be placed across the patient's chest, and a group of ten measurement electrodes that can be attached to the patient's limbs. The measurement electrodes for ECG data acquisition can include a conducting or electrolytic gel (e.g., Ag/AgCl gel) to provide a continuous, electrically-conductive path between the skin and the electrodes. Such "wet" electrodes can reduce the impedance at the electrode-skin interface, thereby facilitating the acquisition of a low-noise ECG signal. All of the measurement electrodes can be connected to a device where signals from the measurement electrodes can be transmitted for storage, processing, and/or displaying. Devices with numerous "wet" electrodes coupled to the user's chest and limbs are invasive, may be difficult to operate for a layperson, and the result ECG waveform may be difficult to interpret. As a result, ECG measurements and analysis may limit the usage of ECG devices to a medical setting or by medical professionals.

One method of measuring an ECG signal is to use dry electrodes that make contact with two areas of a patient, often times on opposite sides of the heart (e.g., on each of the user's hands). On a mobile device (e.g., a wearable device), ECG electrodes can be placed on the device such that the user can make contact with two electrodes. Exposed electrodes, however, can be susceptible to galvanic corrosion.

SUMMARY

This relates to devices and methods of reducing galvanic corrosion of external electrodes (e.g., electrodes used for the measurement of physiological signals, such as an ECG signals). In some examples, protective circuitry, such as a switching circuit, can be used to reduce galvanic corrosion. In a first mode of operation (e.g., corresponding to measurement by the physiological sensing system), the switching circuit can provide a low-impedance path (e.g., from an external electrode to ground). In a second mode of operation (e.g., corresponding to non-measurement by the physiological sensing system), the switching circuit can provide a high-impedance path to reduce leakage currents (e.g., between the external electrode and ground), and thereby reduce galvanic corrosion.

BRIEF DESCRIPTION OF THE DRAWINGS

FIGS. 5A-5I illustrate exemplary configurations for implementing protective circuitry according to examples of the disclosure.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to devices and methods of reducing galvanic corrosion of external electrodes (e.g., electrodes used for the measurement of physiological signals, such as an ECG signals). In some examples, protective circuitry, such as a switching circuit, can be used to reduce galvanic corrosion. In a first mode of operation (e.g., corresponding to measurement by the physiological sensing system), the switching circuit can provide a low-impedance path through the switching circuit (e.g., from an external electrode to ground). In a second mode of operation (e.g., corresponding to non-measurement by the physiological sensing system), the switching circuit can provide a high-impedance path to reduce leakage currents (e.g., between the external electrode and ground), and thereby reduce galvanic corrosion. Unless otherwise specified, it should be understood that high-impedance and low-impedance pathways are relative terms (e.g., the high-impedance path has a higher impedance than the low impedance path). In some examples, the high-impedance path can be greater than 1 kΩ and the low-impedance path can be less than 1 kΩ. In some examples, the impedance of the high-impedance path can be one or more orders of magnitude greater than the low impedance path (e.g., 10x, 100x, etc.).

Figure 1A:
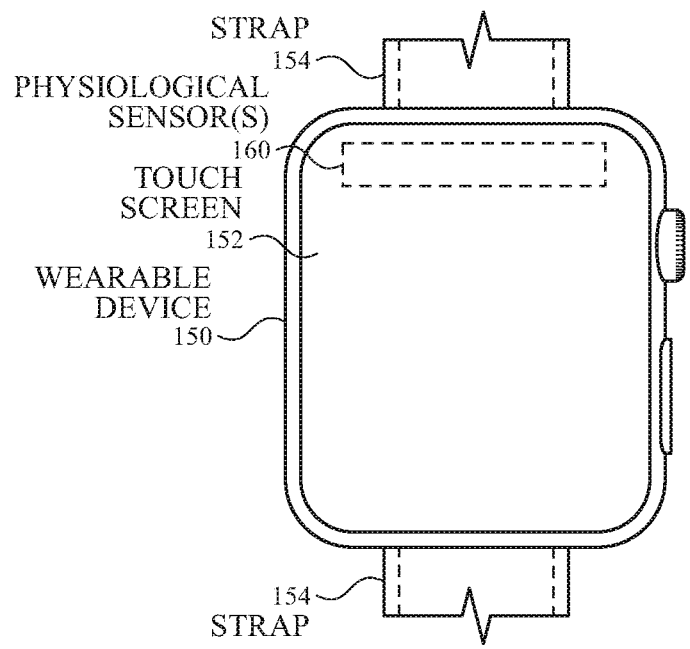
FIGS. 1A-1B illustrate example systems including a physiological sensor in which protective circuitry according to examples of the disclosure may be implemented.
Figure 1B:
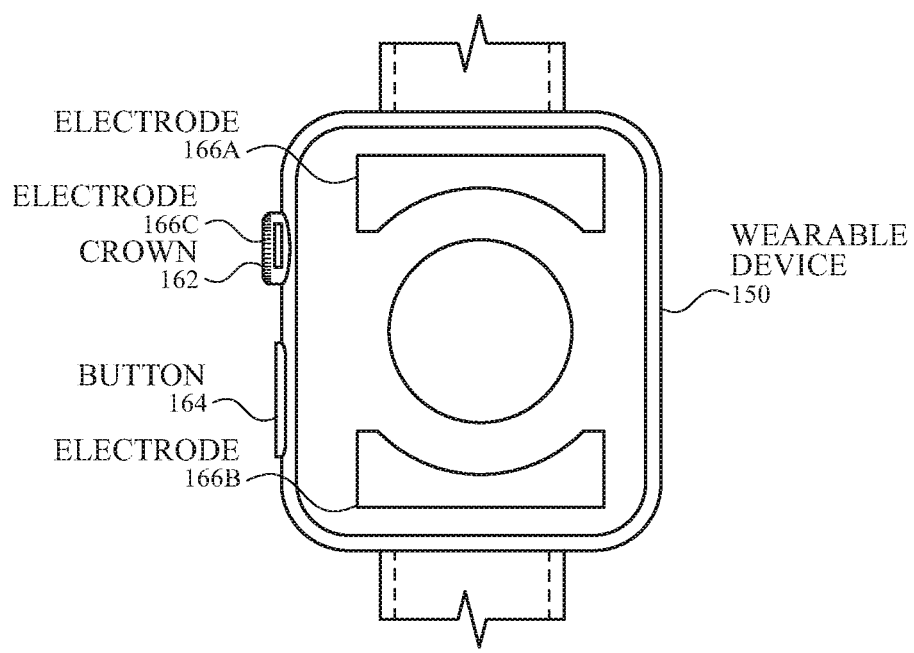

FIGS. 1A-1B illustrate example systems including a physiological sensor and in which protective circuitry according to examples of the disclosure may be implemented. FIG. 1A illustrates an example wearable device 150 (e.g., a watch) that includes an integrated touch screen 152 and physiological sensor(s) 160 (e.g., an ECG sensing system including one or more measurement electrodes, one or more reference electrodes, and processing circuitry coupled to the electrodes). FIG. 1B illustrates an example view of the back side of wearable device 150 that includes a plurality of electrodes 166A-C of physiological sensor 160. Some or all of electrodes 166A-C can be exposed externally from the housing of wearable device 150. Physiological sensor 160 can include electrode 166C implemented in crown 162 of wearable device 150, an electrode implemented in button 164 of wearable device 150 (not shown), electrode 166A on the back side of wearable device 150 and/or electrode 166B on the backside of wearable device 150. In some examples, the physiological sensor 160 can include a measurement electrode (e.g., electrode 166C in crown 162), a first reference electrode (e.g., electrode 166A on the backside of wearable device 150) and a second, ground reference electrode (e.g., electrode 166B on the backside of wearable device 150). In some examples, the physiological sensor 160 can include a measurement electrode in button 164 in addition to or instead of measurement electrode 166C in crown 162. In some examples, the physiological sensor 160 can include more than one measurement electrode and more (or fewer) than two reference electrodes. It is understood that the above physiological sensor(s) can be implemented in other wearable and non-wearable devices, including dedicated devices for the acquisition and/or processing of physiological signals (e.g., ECG signals). It is understood that although mobile device 136 and wearable device 150 include a touch screen, the protective circuitry described herein can be applied to a device without or without a touch-sensitive or non-touch-sensitive display. Additionally it is understood that although the disclosure herein primarily focuses on ECG systems protective circuitry for electrodes of ECG systems, the disclosure can also applicable to other applications including external electrodes.

In some examples, the electrodes of physiological sensors 160 can be dry electrodes which can be measurement electrodes configured to contact a skin surface and capable of obtaining an accurate signal without the use of a conducting or electrolytic gel. In some variations, one or more reference electrodes may be located on a wrist-worn device, such as a bracelet, wrist band, or watch, such that the reference electrodes can contact the skin in the wrist region, while one or more measurement electrodes can be configured to contact a second, different skin region (e.g., a finger of a hand opposite the wrist wearing the wrist-worn device). In some examples, the measurement electrode(s) can be located on a separate component from the reference electrode(s). In some examples, some or all of the measurement electrode(s) can be located on a wrist or finger cuff, a fingertip cover, a second wrist-worn device, a region of the wrist-worn device that can be different from the location of the reference electrode(s), and the like. In some examples, one or more electrodes (e.g., reference electrode or measurement electrode) may be integrated with an input mechanism of the device (e.g., a rotatable input device, a depressible input device, or a depressible and rotatable input device, for example), as shown in FIG. 1B. One or more electrical signals measured by the one or more measurement electrodes can be measured and processed as described in more detail herein.

Figure 2:
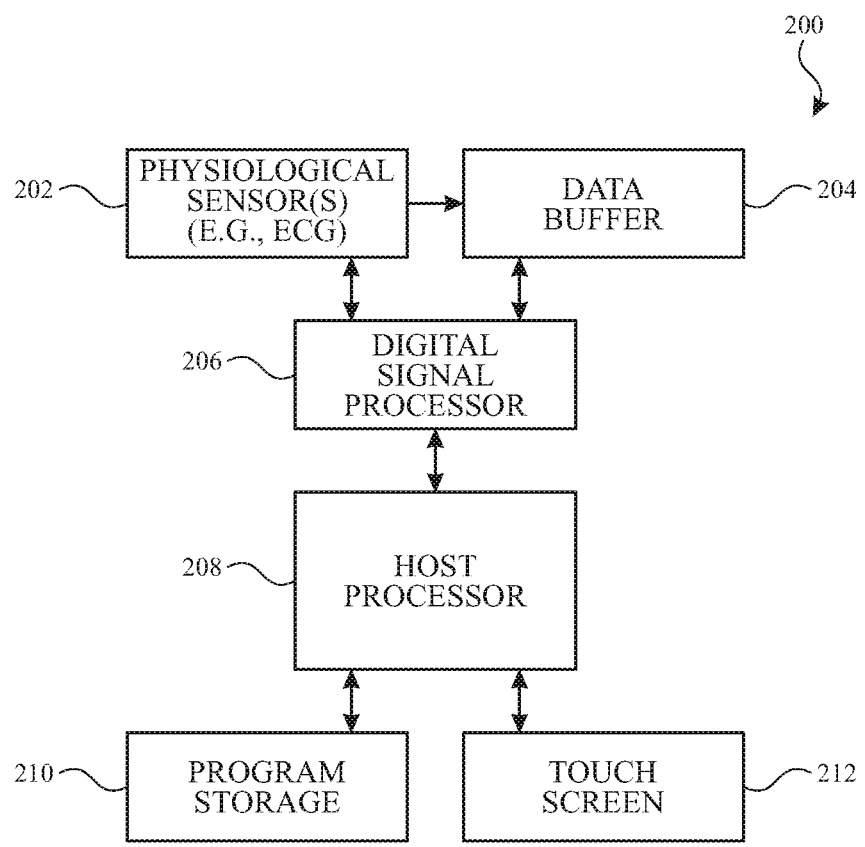
FIG. 2 illustrates a block diagram of an example computing system that illustrates one implementation of physiological signal processing according to examples of the disclosure.

FIG. 2 illustrates a block diagram of an example computing system 200 that illustrates one implementation of physiological signal processing according to examples of the disclosure. Computing system 200 can be included in, for example, wearable device 150 or any mobile or non-mobile, wearable or non-wearable computing device for physiological signal analysis and/or display. Computing system 200 can include one or more physiological sensors 202 (e.g., ECG sensors) including one or more electrodes to measure electrical signals (e.g., ECG signals) from a person contacting the ECG sensor(s) electrodes, data buffer 204 (or other volatile or non-volatile memory or storage) to store temporarily (or permanently) the physiological signals from the physiological sensors 202, digital signal processor (DSP) 206 to analyze and process the physiological signals, host processor 208, program storage 210, and touch screen 212 to perform display operations (e.g., to display real-time ECG signals). In some examples, touch screen 212 may be replaced by a non-touch sensitive display or the touch and/or display functionality can be implemented in another device.

Host processor 208 can be connected to program storage 210 to execute instructions stored in program storage 210 (e.g., a non-transitory computer-readable storage medium). Host processor 208 can, for example, provide control and data signals to generate a display image on touch screen 212, such as a display image of a user interface (UI). Host processor 208 can also receive outputs from DSP 206 (e.g., an ECG signal) and performing actions based on the outputs (e.g., display the ECG signal, play a sound, provide haptic feedback, etc.). Host processor 208 can also receive outputs (touch input) from touch screen 212 (or a touch controller, not-shown). The touch input can be used by computer programs stored in program storage 210 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 220 can also perform additional functions that may not be related to touch processing and display.

Note that one or more of the functions described herein, including operating a protective switching circuit or the measurement and processing of physiological signals, can be performed by firmware stored in memory (e.g., in DSP 206) and executed by one or more processors (in DSP 206), or stored in program storage 210 and executed by host processor 208. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

It is to be understood that the computing system 200 is not limited to the components and configuration of FIG. 2, but can include other or additional components (or omit components) in multiple configurations according to various examples. For example, an analog-to-digital converter (ADC) may be added between physiological sensor 202 and DSP 206 to convert the signals to the digital domain or touchscreen 212 can be omitted and the ECG signal or other information from the analysis and processing can be relayed to another device (e.g., a tablet, laptop, smartphone, computer, server, etc.) via wired or wireless connection that can include a display or other feedback mechanism for outputting a visual representation of the data or other notifications or information. Additionally, the components of computing system 200 can be included within a single device, or can be distributed between multiple devices.

Returning back to physiological sensor(s) 202, the mobile or wearable device (or other device) may comprise one or more of measurement electrodes and one or more reference electrodes. Physiological sensors 202 can be in communication with DSP 206 to acquire physiological signals and transmit the signals to DSP 206. In some examples, the physiological signals can be acquired by data buffer 204 and the DSP 206 can acquire a buffered sample of the physiological waveform (e.g., 3 second sample, 5 second sample, 10 second sample, 30 second sample, 60 second sample). In some examples, data buffer 204 can be implemented as part of DSP 206. It should be understood that although a DSP is described, other processing circuits could be used to implement the analysis and processing described herein including a microprocessor, central processing unit (CPU), programmable logic device (PLD), and/or the like.

Although the examples and applications of contact detection and processing devices and methods are described in the context of generating a complete ECG waveform, it should be understood that the same or similar devices and methods may be used to collect and process data from the plurality of measurement electrodes and may or may not generate an ECG waveform. For example, the signals from the physiological sensors 202 may facilitate the monitoring of certain cardiac characteristics (e.g., heart rate, arrhythmias, changes due to medications or surgery, function of pacemakers, heart size, etc.) and/or ECG waveform characteristics (e.g., timing of certain waves, intervals, complexes of the ECG waveform) by the DSP and/or user without generating a complete ECG waveform. In some examples, the controller may generate a subset of the ECG waveform (e.g., one or more of the P wave, QRS complex, PR interval, T wave, U wave). Moreover, examples of the disclosure include protective circuitry configured for electrodes in other types of application outside of physiological signal measurement applications.

Figure 3:
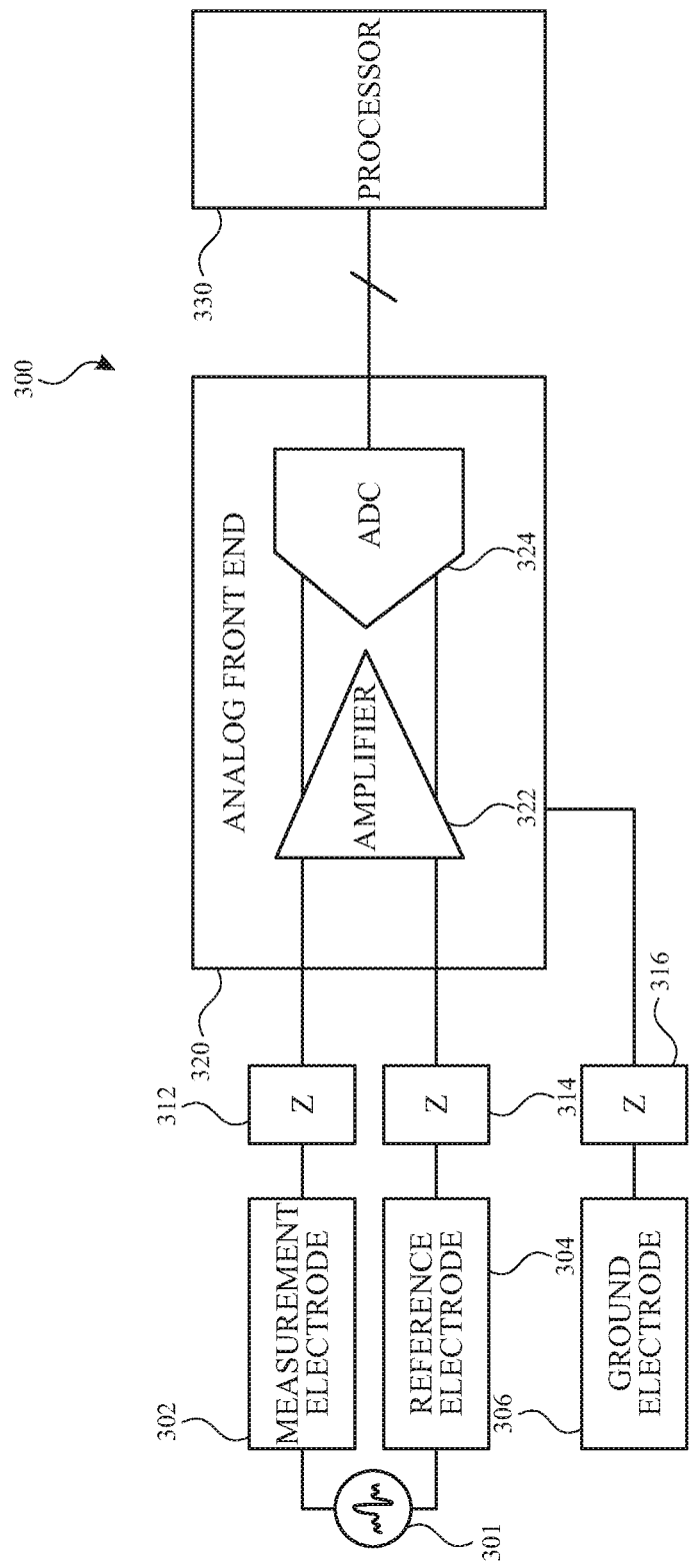
FIG. 3 illustrates an example system for measuring physiological signals according to examples of the disclosure.

FIG. 3 illustrates an example system for measuring physiological signals according to examples of the disclosure. In FIG. 3, circuit 300 can include processor 330 (e.g., corresponding to DSP 206 and/or host processor 208), analog front end (AFE) 320, measurement electrode 302 (e.g., corresponding to measurement electrode 166C), reference electrode 304 (e.g., corresponding to reference electrode 166A and/or reference electrode 166B), and ground electrode 306 (e.g., corresponding to reference electrode 166A and/or reference electrode 166B). In some examples, circuit 300 can be integrated in a mobile device (e.g., a wearable device 150). In some examples, analog front end 320 can include amplifier 322 and analog-to-digital converter (ADC) 324. Amplifier 322 can be a differential amplifier coupled to measurement electrode 302 (e.g., on the inverting input or on the non-inverting input) and to reference electrode 304 (e.g., on the non-inverting input or on the inverting input). In some examples, ground electrode 306 can be coupled to analog front end 320 to provide a shared ground reference between circuit 300 and ground electrode 306 (e.g., ground electrode 306 can provide a system ground reference voltage). Although a shared ground between the physiological signal sensing system and the circuit 300 can be used, in some examples, ground electrode 306 for the physiological signal sensing system can be coupled to a different node (with a different voltage than) ground of circuit 300. In some examples, circuit 300 can include networks 312, 314, and 316, along the signal paths for the measurement electrode 302, reference electrode 304, and ground electrode 306, respectively. In some examples, networks 312, 314, and 316 can include circuit components (e.g., resistors, capacitors, inductors and/or diodes) and/or can include impedances inherent in circuit 300 (e.g., routing impedances, parasitic impedances, etc.). In some examples, networks 312, 314 and 316 can provide electrostatic discharge (ESD) protection for the circuit 300 and/or provide safety by limiting or preventing electrical currents being applied to the user's skin and/or preventing unexpected or unintentional external signals from entering the device and causing damage. In some examples, the ESD protection can be integrated into the analog front end 320 (as opposed to being implemented discretely). In some examples, amplifier 322 can output an amplified differential signal and analog-to-digital converter 324 can convert the amplified differential signal into a digital signal. In some examples, amplifier 322 can output an amplified single-ended output. In some examples, the output of analog-to-digital converter 324 can be a multi-bit signal (e.g., 8 bits, 12 bits, 24 bits, etc.) coupled to processor 330. The multi-bit signal can be transmitted from analog front end 320 to processor 330 serially or in parallel. In some examples, analog-to-digital converter 324 can be a differential analog-to-digital converter and convert a differential analog input to a digital output. In some examples, analog-to-digital converter 324 can be single-ended and convert a single-ended analog input to a digital output.

In some examples, a user can wear the wearable device, such as a watch, including circuit 300. For example, wearable device 150 can be worn on the wrist of a user. In such examples, reference electrode 304 and ground electrode 306 can contact with the wrist of the user when worn. When a user touches measurement electrode 302 (e.g., electrode 166C of crown 162 of wearable device 150), measurement electrode 302 can receive a physiological signal from the user. In some examples, the measured physiological signal can be a clinically accurate waveform (e.g., meets the specifications for a clinically accurate waveform) due to the reliable contact between the finger and measurement electrode 302. In FIG. 3, the user is represented as physiological signal source 301. In some examples, when the user touches measurement electrode 302, a path can be created through physiological signal source 301 from measurement electrode 302 to reference electrode 304 and/or ground electrode 306 (e.g., from the user's finger contacting measurement electrode 302 across the user's chest to the wrist upon which the user is wearing the wearable device and to reference electrode 304 and/or ground electrode 306). In some examples, contacting measurement electrode 302 can cause circuit 300 to measure a physiological signal from physiological signal source 301.

It is understood, that in some examples, when a user contacts the housing of wearable device 150 with their finger instead of crown 162, that the acquired physiological signal can be attenuated as compared to physiological signal acquired when the finger contacts crown 162 (e.g., 5%, 10%, 20% attenuation, etc.). Additionally or alternatively, the physiological signal may be unstable, noisy, and/or the amplitude and attenuation can vary non-deterministically. Additionally or alternatively, the measured physiological signal may not be a clinically accurate waveform (e.g., does not conform to the specifications for a clinically accurate waveform) and can be difficult to interpret or lead to misinterpretation of the physiological signal (e.g., as compared with physiological signal acquired when the finger contacts crown 162). In some examples, contact detection circuits and methods (e.g., signal quality checks to detect contact between a user's finger and the measurement electrode and/or between a user's wrist and the reference electrode) can be used to avoid acquiring and/or processing and/or presenting to a user physiological signal waveforms that can be attenuated, unstable, or otherwise unreliable. In some examples, the user can be notified about poor contact resulting in failure of signal quality checks and/or be provided with instructions for adjusting contact between the user and one or more electrodes.

Figure 4A:
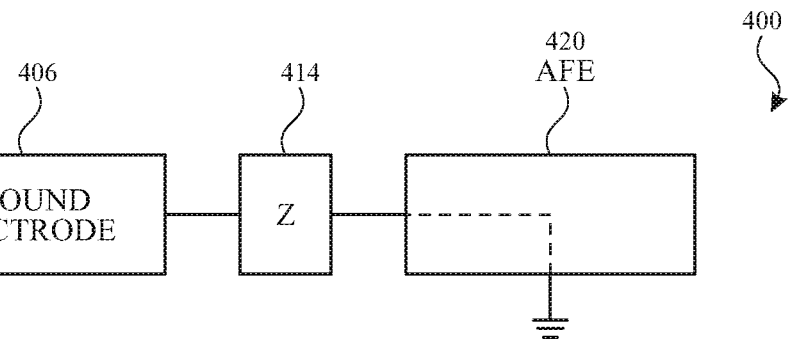
FIGS. 4A-4D illustrate exemplary configurations of an exemplary electrode and its coupling to ground according to examples of the disclosure.

FIGS. 4A-4D illustrate exemplary configurations of an exemplary electrode and its coupling to ground according to examples of the disclosure. FIG. 4A illustrates an exemplary configuration 400 including ground electrode 406 (e.g., corresponding to ground electrode 306), network 414 (e.g., corresponding to network 314) and AFE 420 (corresponding to AFE 320). AFE 420 can be representative of an integrated circuit including a connection to ground of a device (e.g., wearable device 150). It should be understood that configuration 400 can represent a portion of a physiological sensing circuit (e.g., corresponding to circuit 300). As shown in the configuration of FIG. 4A, ground electrode 406 can be electrically coupled to ground of the device. As used herein, an electrical component "coupled to" or "connected to" another electrical component encompasses a direct or indirect connection providing electrical path for communication or operation between the coupled components. Thus, for example, ground electrode 406 may be coupled to ground (e.g., a ground node) indirectly via network 414 and/or additional circuitry of AFE 420, but an electrical path between ground electrode 406 and ground can be provided.

Ground electrode 406 can be an external contact (e.g., an electrode of an ECG sensor) with a relatively low-impedance path to ground. As a result, when exposed to liquids with electrolyte solutions (e.g., sweat, soapy water, etc.), the electrode (and other external contacts) can be subject to galvanic corrosion. This galvanic corrosion can reduce the lifetime of the device including ground electrode 406 and/or require maintenance more frequently to replace corroded components. Protective circuitry, including a switching circuit, can be introduced to reduce or avoid this galvanic corrosion. In some examples, to reduce or avoid this galvanic corrosion, it can be advantageous to replace the relatively low-impedance path to ground with a relatively high-impedance path to ground (i.e., with low leakage currents). For example, a high-impedance switching circuit 402 can be introduced between ground electrode 406 and ground, as shown in configurations 410, 430 and 440 in FIGS. 4B-4D. As such, galvanic corrosion can be mitigated while switching circuit 402 operates in an "open" state due to the high-impedance between ground electrode 406 and ground (e.g., while the physiological signal is not being measured). The galvanic corrosion, however, may occur while switching circuit 402 operates in a "closed" state due to the low-impedance between ground electrode 406 and ground (e.g., while the physiological signal is being measured). By reducing the time during which galvanic corrosion may occur (e.g., restricting to the times during which physiological sensing via measurement electrode 302, reference electrode 304 and/or ground electrode 306 occurs), the lifetime of the device can be extended compared with the lifetime of the device without a switching circuit.

Figure 4B:
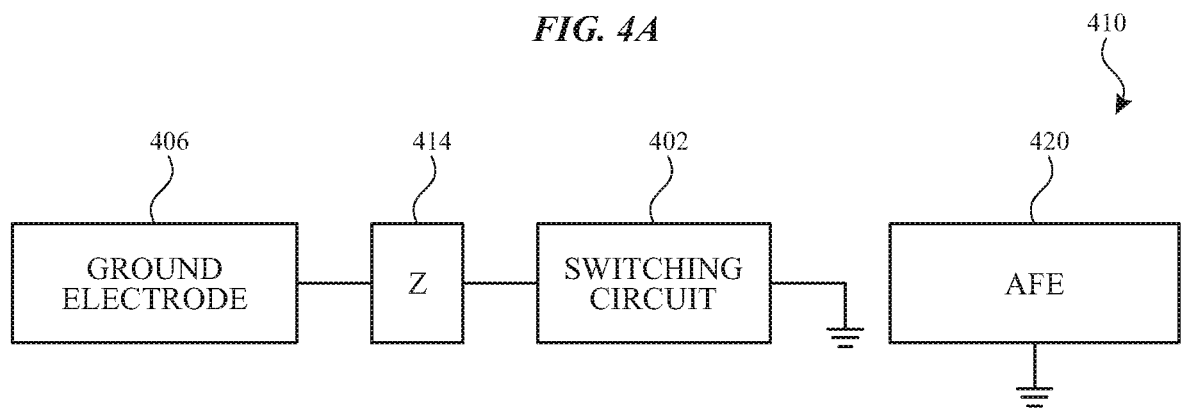
Figure 4C:
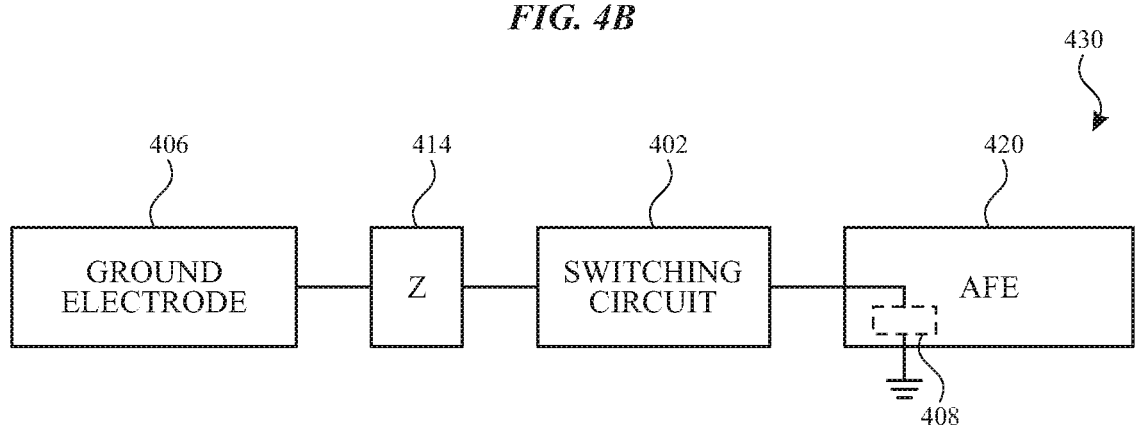
Figure 4D:
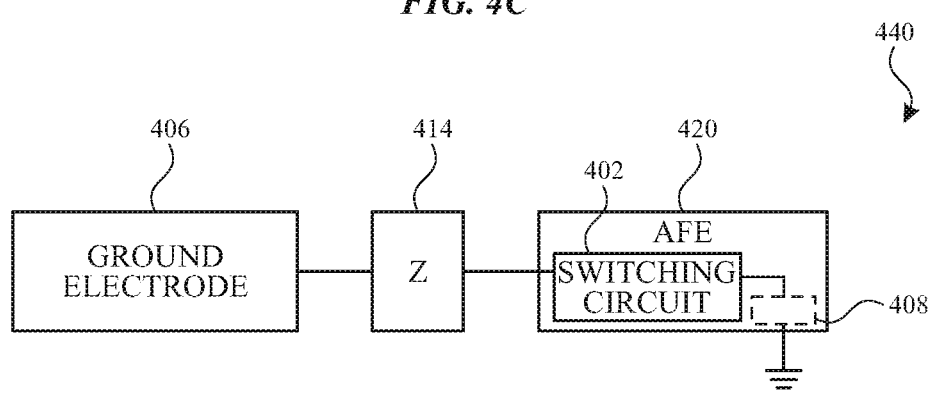

FIGS. 4B-4D illustrate exemplary configurations 410, 430 and 440 according to examples of the disclosure. Configurations 410, 430 and 440 can also include ground electrode 406, network 414 and AFE 420. However, unlike configuration 400 of FIG. 4A, configurations 410, 430 and 440 can include switching circuit 402 between ground electrode 406 and ground. In some examples (e.g., as illustrated in FIGS. 4B-4C), the switching circuit can be implemented separate from AFE 420 (e.g., on a circuit board separate from of an integrated circuit including AFE 420). In some examples (e.g., as illustrated in FIG. 4D), the switching circuit can be integrated into AFE 420 (integrated into the integrated circuit including AFE 420). Additionally, in some examples, additional circuitry 408 (e.g., switches, resistors, etc.) can be incorporated into the path between switching circuit 402 and ground. The additional circuitry 408 can be integrated into AFE 420 as shown in FIGS. 4C-4D, in some examples. In some examples, the additional circuitry 408 can be implemented separate from AFE 420.

Although switching circuitry can be implemented to provide a relatively high-impedance path (e.g., with leakage currents less than a threshold, such as <10nA across process, voltage, and temperature), the high-impedance of the switching circuit can cause the external electrode to float relative to system ground. As a result of the size characteristics of the external electrode (e.g., its surface area), the electrode can pick up noise from the operating environment (e.g. from lights, power cables, etc.), which can build up to a relatively large voltage and cause electrical overstress of the physiological sensing circuitry. To avoid or reduce the effects of electrical overstress, the protective circuit (e.g., the switching circuit) can be designed or selected to tolerate relatively-high electrical overstress events that may occur for sustained durations (e.g., different than electrostatic discharge (ESD) events). Additionally, the switch can be bipolar to reduce leakage currents (high impedance) for both negative and positive voltage swings at the electrode.

Figures 5A, 5B:
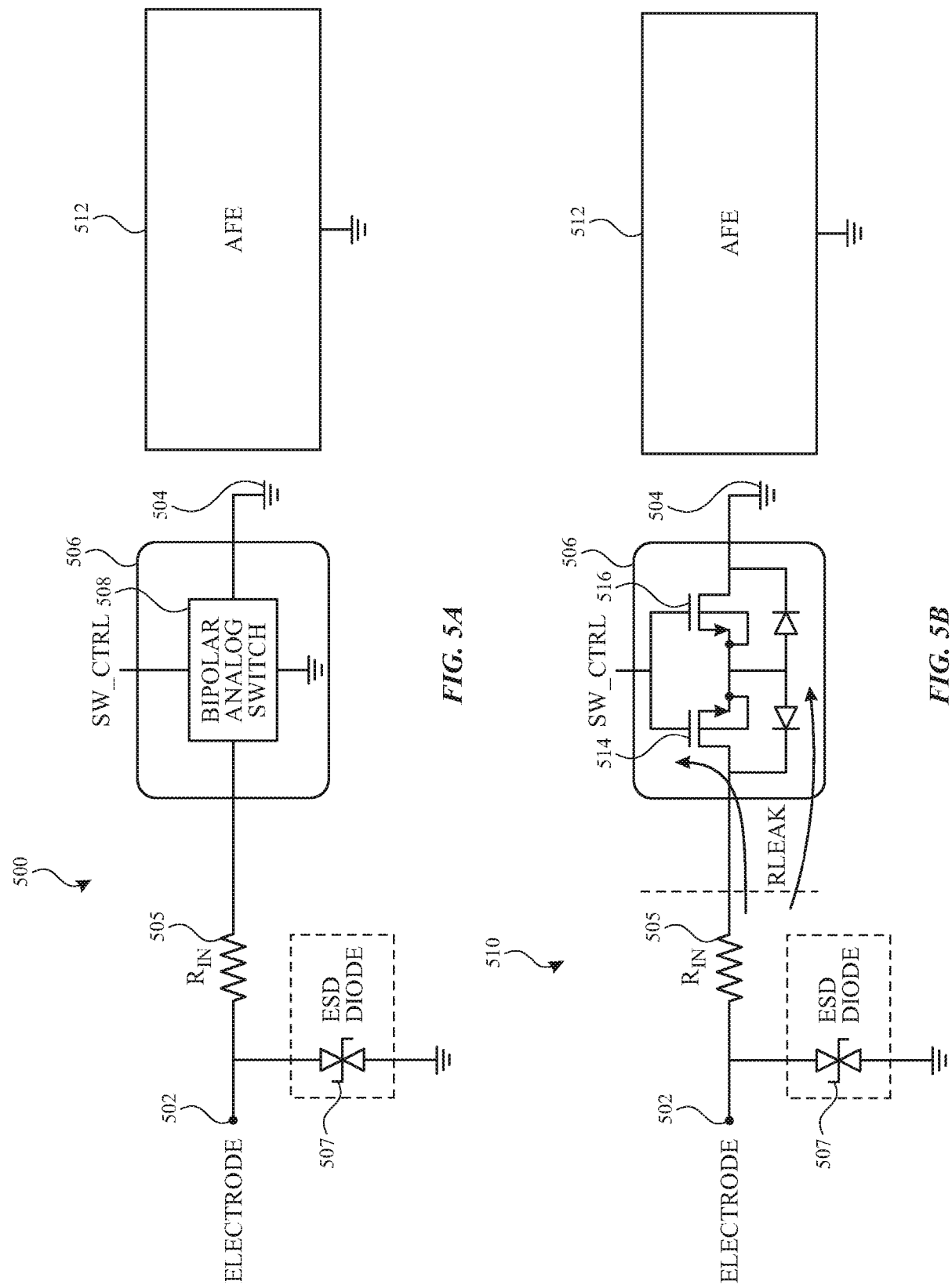

FIGS. 5A-5I illustrate exemplary configurations for implementing protective circuitry according to examples of the disclosure. FIG. 5A illustrates configuration 500 coupling electrode 502 (e.g., corresponding to ground electrode 406) to ground 504 via a switching circuit 506 (e.g., corresponding to switching circuit 402). In addition to switching circuit 506, configuration 500 can include an input network (e.g., corresponding to network 414). The input network can include an input resistor 505 (e.g., to protect a user from voltages from the ECG system in case of a fault) and/or an ESD diode 507 (e.g., to protect against ESD events). Switching circuit 506 can include a bipolar analog switch 508 (e.g., single-pull, single-throw). One side of switching circuit 506 can be coupled to the input network and a second side of switching circuit 506 can be coupled to system ground. The bi-polar analog switch 508 can provide protection against some electrical overstress for both negative and positive voltage swings at the electrode (which can be possible for a physiological signal such as cardiac signals). Additionally, bi-polar analog switch 508 can provide low leakage (and thereby reduce or prevent galvanic corrosion) while switching circuit 506 is in an open or high-impedance state, and provide a low-impedance (e.g., <200 Ω, <100 Ω) while switching circuit 506 is in a closed or low-impedance state. The state of switching circuit 506 can be controlled by a switch control input ("SW CTRL"), which can be provided, for example, by a processor (e.g., DSP 206, host processor 208, etc.). As illustrated in FIG. 5A, the output of switching circuit 506 can be connected to system ground separate from AFE 512 (e.g., as illustrated in configuration 410). In some examples, the connection to system ground can be achieved via AFE 512 (e.g., as illustrated in configuration 430, 440).

FIG. 5B illustrates configuration 510 coupling electrode 502 to ground 504 via a switching circuit 506 (and via an input network including resistor 505 and ESD diode 507). Unlike FIG. 5A, in FIG. 5B, switching circuit 506 can include two n-mos transistors 514 and 516 configured as a shunt switch. The state of switching circuit 506 can be controlled by the switch control input ("SW CTRL"), in a similar manner as described with respect to FIG. 5A. Diodes shown in parallel across n-mos transistors 514 and 516 are for illustration purposes of a leakage pathway through the transistors of switching circuit 506 (e.g., due to parasitic components of the transistors' physical construction), and are not included as discrete components in the switching circuit. As indicated by the reverse orientation of these diodes, the shunt switch can provide bi-polar blocking of leakage currents ("R-leak") through transistors 514 and 516 while switching circuit 506 is in the open, high-impedance state. As illustrated in FIG. 5B, the output of switching circuit 506 can be connected to a system ground node separate from AFE 512 (e.g., as illustrated in configuration 410). In some examples, for example as illustrated in configuration 520 of FIG. 5C, the connection to system ground can be achieved via AFE 512 (e.g., as illustrated in configuration 430, 440). Additionally, in some examples, as shown in FIG. 5C, a bleeder resistor 518 can be added from the output of the switching circuit to system ground to prevent or mitigate an increase in voltage on the input to system ground in AFE 512 (which may potentially damage AFE 512 from electrical overstress), which can otherwise occur due to release of charge accumulated in the open state upon a transition to the closed state.

FIG. 5D illustrates configuration 530 coupling electrode 502 to ground 504 via a switching circuit 506 (and via input network including resistor 505 and ESD diode 507). Unlike FIG. 5B, switching circuit 506 in FIG. 5D can include a p-mos transistor 522 and an n-mos transistor 524 configured as a complimentary series switch. Diodes shown in parallel across p-mos transistor 522 and n-mos transistor 524 are for illustration purposes of a leakage pathway through the transistors of switching circuit 506 (e.g., due to parasitic components of the transistors' physical construction), and are not included as discrete components in switching circuit 506. As indicated by the reverse orientation of these diodes, the complimentary switch can provide bi-polar blocking of leakage currents ("Idss") through transistors 514 and 516 while switching circuit 506 is in the open, high-impedance state. In some examples, the state of switching circuit 506 can be controlled by complementary power rails, VgateP and VgateN. For example, VgateP and VgateN can be supply rails provided from the ECG sensing system (e.g., from the integrated circuit including AFE 512). While power rails VgateP and VgateN are supplied to the respective gates of transistors 522 and 524, switching circuit 506 can be in a closed, low-impedance state. While power rails VgateP and VgateN are powered off, the gates of transistors 522 and 524 can be pulled down to ground (e.g., through weak pull-down resistors, as shown), and switching circuit 506 can be in an open, high-impedance state.

Figure 5E:
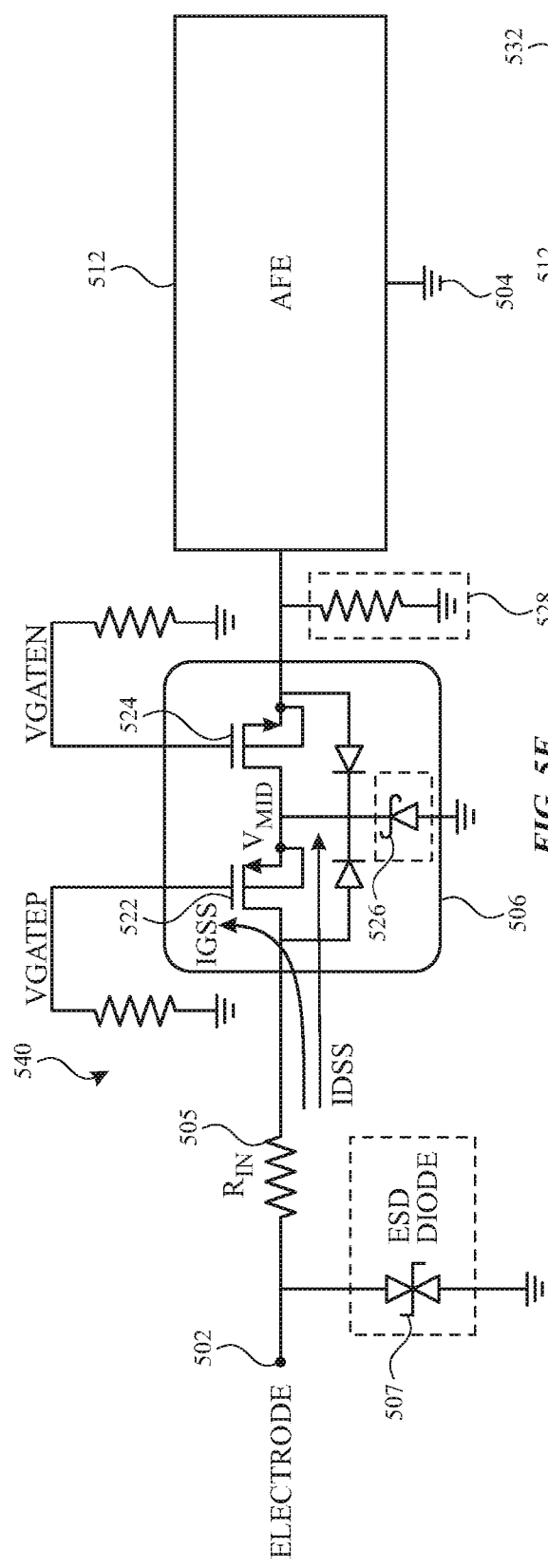

As illustrated in FIG. 5D, the output of switching circuit 506 can be connected to system ground separate from AFE 512 (e.g., as illustrated in configuration 410). In some examples, for example, as illustrated in configuration 540 of FIG. 5E, the connection to system ground can be achieved via AFE 512 (e.g., as illustrated in configuration 430, 440). Additionally, in some examples, as shown in FIG. 5E, a Zener diode 526 can be added between the midpoint of transistors 522 and 524 to clamp the voltage at the midpoint. Clamping the voltage can provide further overload protection to the gate-source junction of p-mos transistor 522 and limit that maximum voltage appearing at the pin of the integrated circuit including AFE 512 coupled to the output of switching circuit 506. Additionally, in some examples, as shown in FIG. 5E, a resistor 528 can be added from the output of the switching circuit to system ground to prevent or mitigate an increase in voltage on the input to system ground in AFE 512 (which may potentially damage AFE 512 from electrical overstress). Although resistor 528 is shown outside of AFE 512, in some examples, resistor 528 can be integrated into AFE 512.

It should be understood that the order of the p-mos and n-mos transistors in the complementary series switch of FIG. 5D (i.e., p-mos coupled to the electrode and n-mos coupled to the ground) can provide benefits over the reverse configuration. For example, using an n-mos transistor coupled to the electrode can allow negative voltages to be passed and can prevent the use of a negative voltage clamp (e.g., such as Zener diode 526 of FIG. 5E). Additionally, if the p-mos and n-mos transistors are used in the reverse configuration, the source and drain of the p-mos transistor can be reversed and cause the p-mos transistor to turn on, rather than block, negative voltages and leakage currents.

Figure 5F:
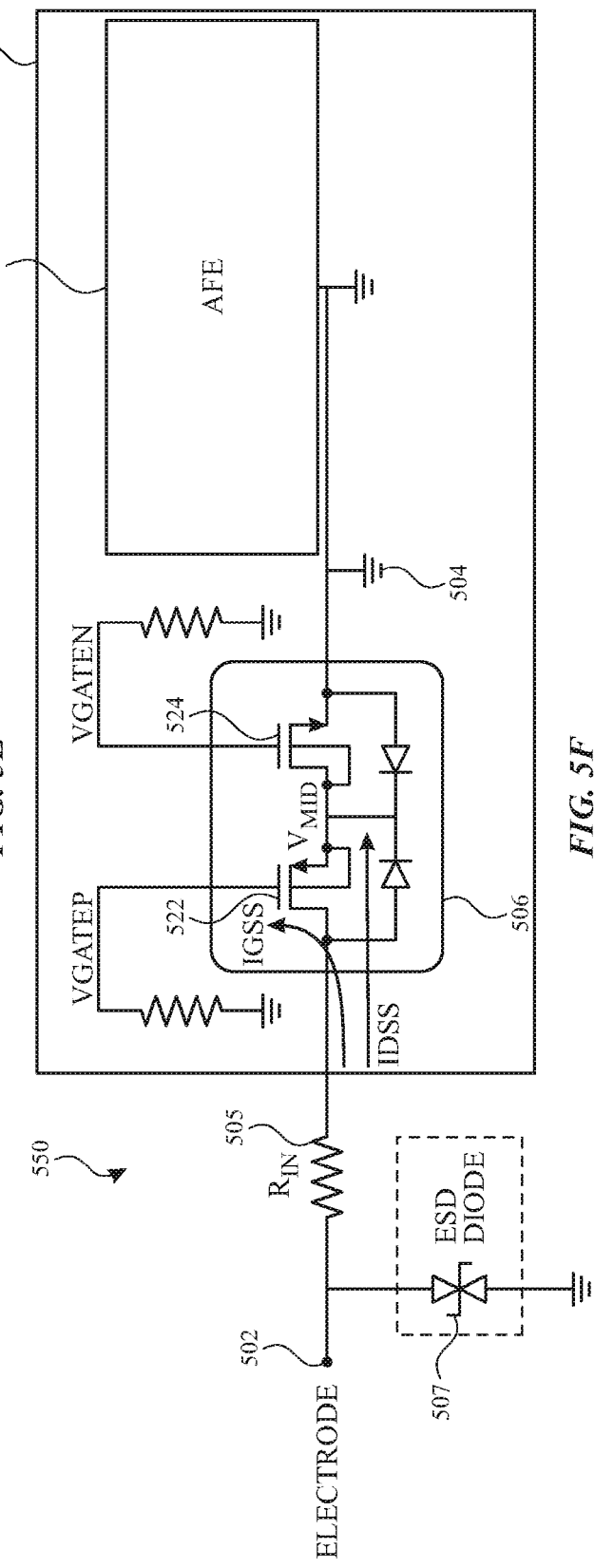
Figure 5G:
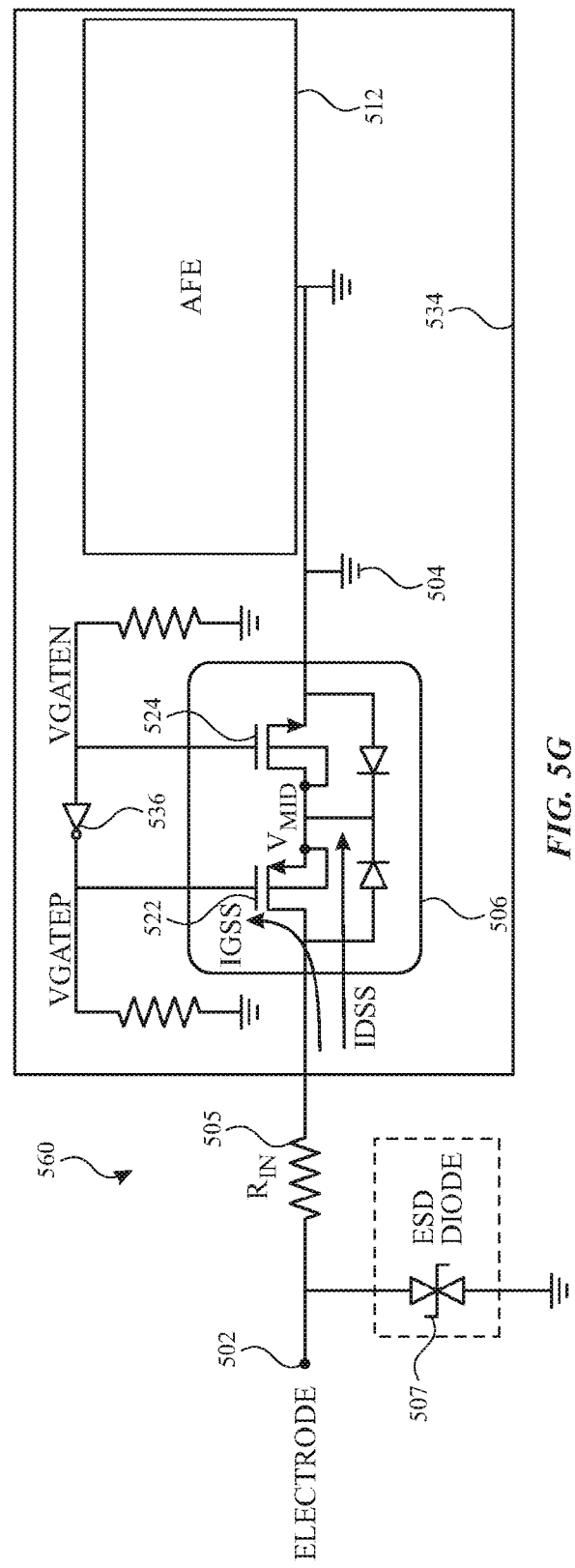

Although the switching circuits 506 of FIGS. 5A-5E are illustrated separate from AFE 512, it should be understood that, in some examples, switching circuits 506 can be integrated into an integrated circuit including AFE 512. FIGS. 5F-5G illustrate switching circuits integrated with an AFE in an integrated circuit according to examples of the disclosure. For example, FIG. 5F illustrates configuration 550 including an integrated circuit 532 that includes switching circuit 506 (e.g., corresponding to the complementary series switch of FIG. 5D) and that includes AFE 512. Integrated circuit 532 can also include other circuitry including, but not limited to, processing circuitry (e.g., DSP 206) and power management circuitry (e.g., to generate supply rails VgateP and VgateN). In some examples, as shown in configuration 560 in FIG. 5G, switching circuit 506 (e.g., corresponding to the complementary series switch of FIG. 5D) and AFE 512 can be integrated into integrated circuit 534. Rather than integrated circuit 534 generating both supply rails VgateP and VgateN (e.g., using a negative charge pump (not shown)), in some examples, integrated circuit 534 can generate VgateN, and an inverter circuit 536 can be used to generate VgateP from VgateN.

Figure 5H:
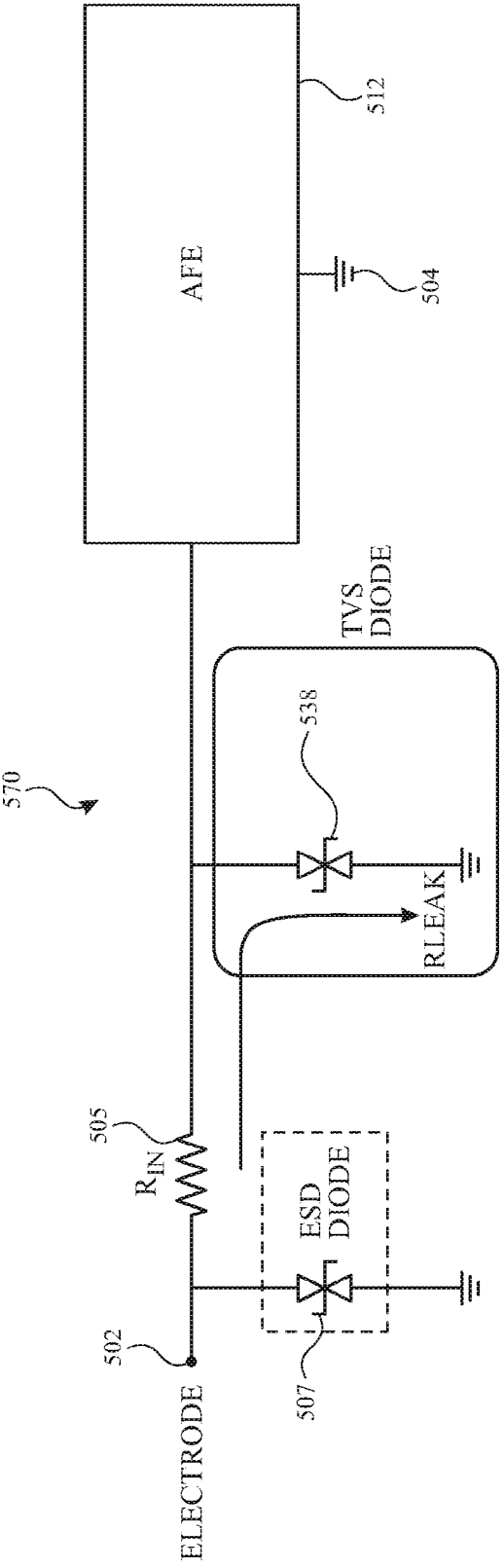
Figure 5I:
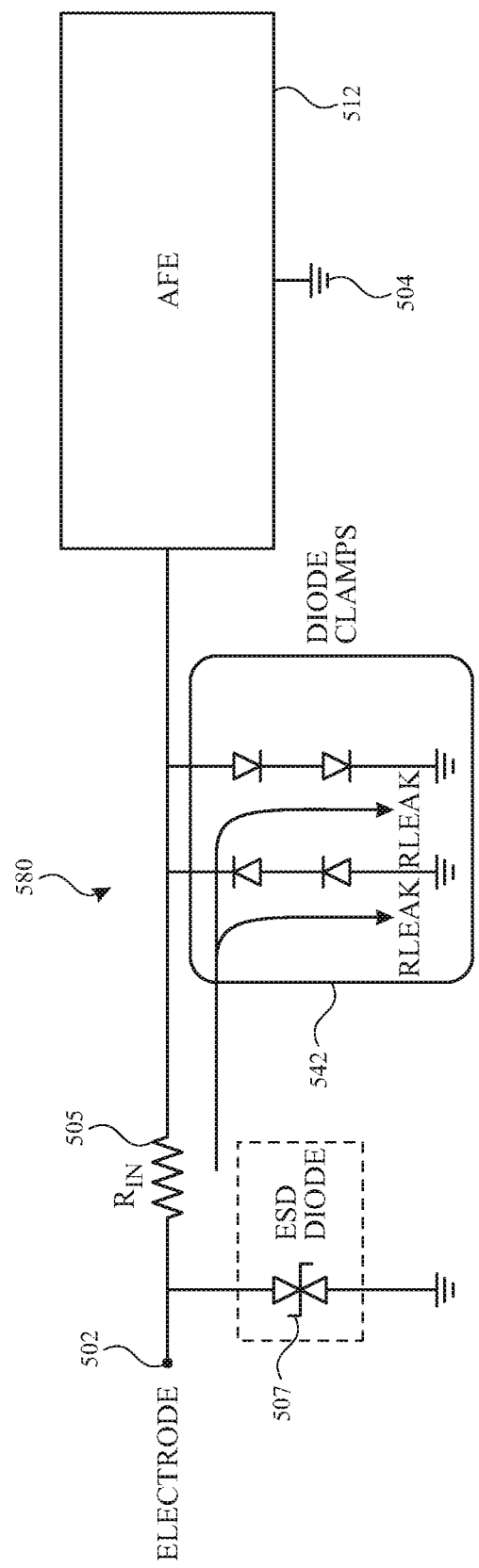

Although FIGS. 5A-5G primarily describe switching circuits and an input network including a resistor and an ESD diode, in some examples, additional circuitry can be included. For example, FIG. 5H illustrates configuration 570 with an input network including a transient-voltage-suppression diode 538 coupled between resistor 505 and to system ground to clamp the voltage input to AFE 512. As another example, FIG. 5I illustrates configuration 580 with an input network including dual-diode clamps 542 coupled between resistor 505 and system ground to clamp the voltage input to AFE 512. For simplicity of illustration and description, a switching circuit (e.g., such as those described with respect to FIGS. 5A-5G) is not shown between input network and AFE 512. However, it should be understood that a switching circuit as described herein can be implemented between the input network and AFE 512 (or integrated into AFE 512) in configurations 570 and 580.

It should be understood that the configurations of FIGS. 5A-5I are exemplary and that modifications (e.g., adding or removing circuit components) are within the scope of the disclosure. For example, one or more of the above switching circuits (e.g., a complimentary series switch and a shunt switch in series) can be combined in series between an external electrode and the system ground. Additionally, circuitry to limit leakage currents outside of the switching circuitry (e.g., diode clamps, bleeder resistors, etc.) can be added or removed as required to meet design specifications.

Figure 6:
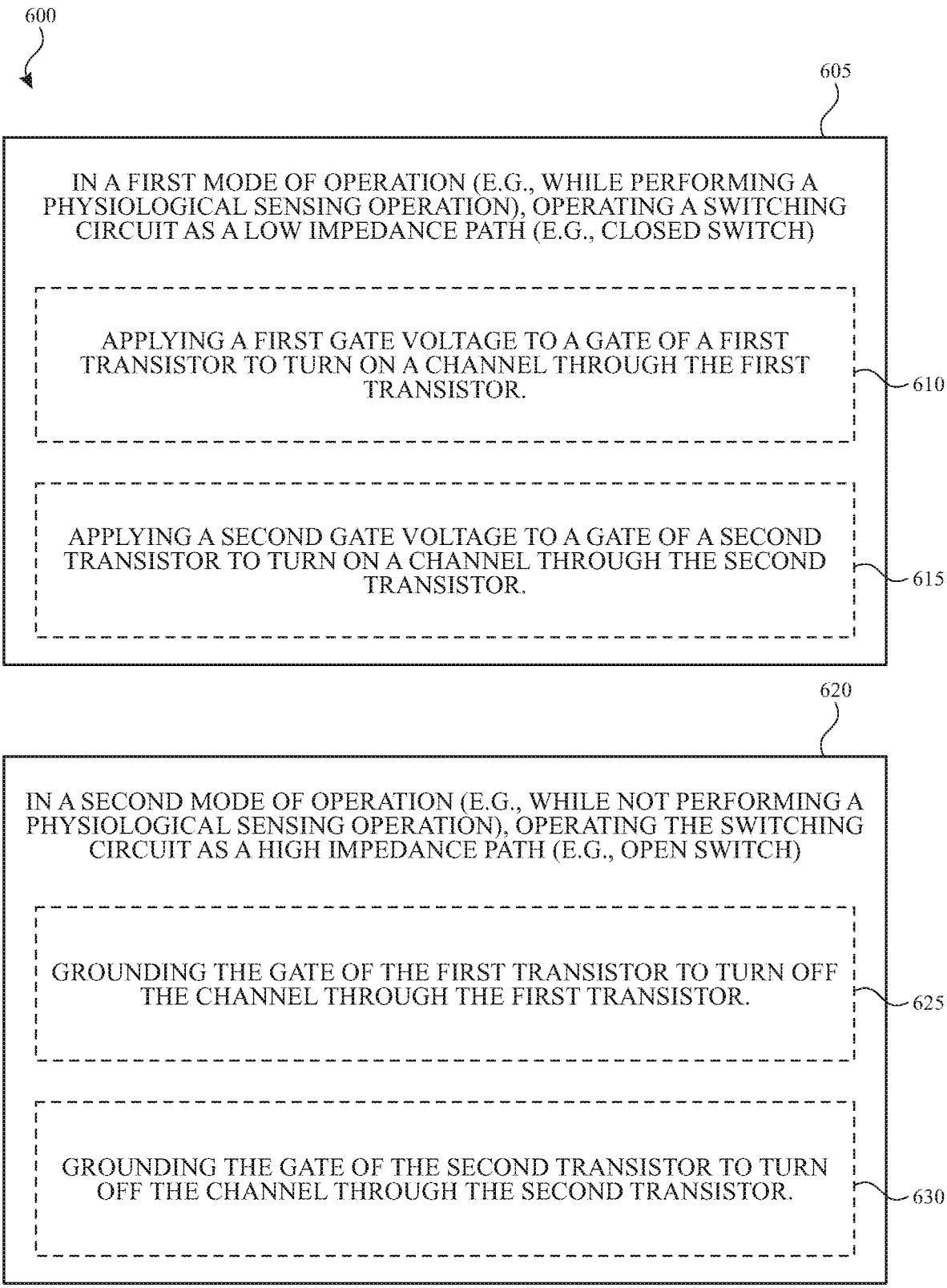
FIG. 6 illustrates an exemplary process of operating a switching circuit according to examples of the disclosure.

FIG. 6 illustrates an exemplary process 600 of operating a switching circuit (e.g., corresponding to switching circuit 506) according to examples of the disclosure. At 605, in a first mode of operation, the switching circuit can be operated as a low-impedance path (e.g., having a resistance through the switching circuit less than a threshold impedance (<1 kΩ, <500 Ω, <100 Ω, etc.)). At 620, in a second mode of operation, the switching circuit can be operated as a high-impedance path (e.g., having a resistance through the switching circuit greater than a threshold impedance (>1 MΩ, >10 Ω, >10 GΩ, etc.)). In other words, the switching circuit can operate as a closed switch in the first mode of operation, and can operate as an open switch in the second mode of operation.

The mode of operation of the switching circuit can correspond to the mode of operation of the operation of the corresponding electrode. For example, for physiological sensing system measuring ECG signals, the first mode of operation can correspond to performing the physiological sensing operation, and the second mode of operation can correspond to not performing the physiological sensing operation. In some examples, the first mode of operation can also correspond to periods during which the physiological sensing system prepares for, but does not necessarily perform, physiological sensing operations (e.g., the duration of time to set up a physiological sensing session) and/or to periods after the physiological sensing system performs sensing operations (e.g., the duration of time to end a physiological sensing session after the measurements are complete). In some examples, galvanic corrosion can be reduced by operating the switching circuit in the first operating mode (low-impedance) while necessary for physiological signal sensing, and operating the switching circuit in the second operating mode (high-impedance) while physiological signal sensing may not be performed.

In some examples, operating the switching circuit in the first mode of operation and the second mode of operation can include applying logic or gate voltages to control the switching circuit. For example, bipolar analog switch 508 of FIG. 5A can be operated by applying a logic signal to close bipolar analog switch 508 in the first mode of operation and as an open switch in the second mode of operation. In some examples, voltages can be applied to turn on transistors of the switching circuit. For example, at 610, a first gate voltage can be applied to a gate of a first transistor to turn on a channel through the first transistor. At 615, a second gate voltage can be applied to a gate of a second transistor to turn on a channel through the second transistor. Opening a channel through the first and second transistors can cause the switching to operate as a closed switch. For example, complimentary series switch of FIG. 5D can be operated in the first state by applying VgateP to p-mos transistor 522 and VgateN to n-mos transistor 524. Likewise, at 625, the gate of the first transistor can be grounded to turn off the channel through the first transistor. At 630, the gate of the second transistor can be grounded to turn off the channel through the second transistor. Closing the channel through the first and second transistors can cause the switching to operate as an open switch. For example, complimentary series switch of FIG. 5D can be operated in the second state by pulling down the gate of p-mos transistor 522 to ground (e.g., by powering down supply rail of VgateP) and by pulling down the gate of n-mos transistor 524 (e.g., by powering down supply rail of VgateN).

In some examples, the voltages can be supplied by power rails activated for the purposes of physiological signal sensing in order to reduce the control overhead for the switching circuit. For example, power rails corresponding to VgateP and VgateN can be powered up for use in physiological signal sensing operations (or sessions) and powered down outside of these physiological sensing operations (or sessions). As a result, the switching circuit can be operated appropriately to reduce galvanic corrosion outside of the physiological sensing operations without interfering with physiological sensing operations, and without requiring additional switching control functionality. In some examples, the complimentary switch can be controlled by one power rail using an inverter to supply the second gate voltage (e.g., as illustrated in and described with reference to FIG. 5G).

Figure 7:
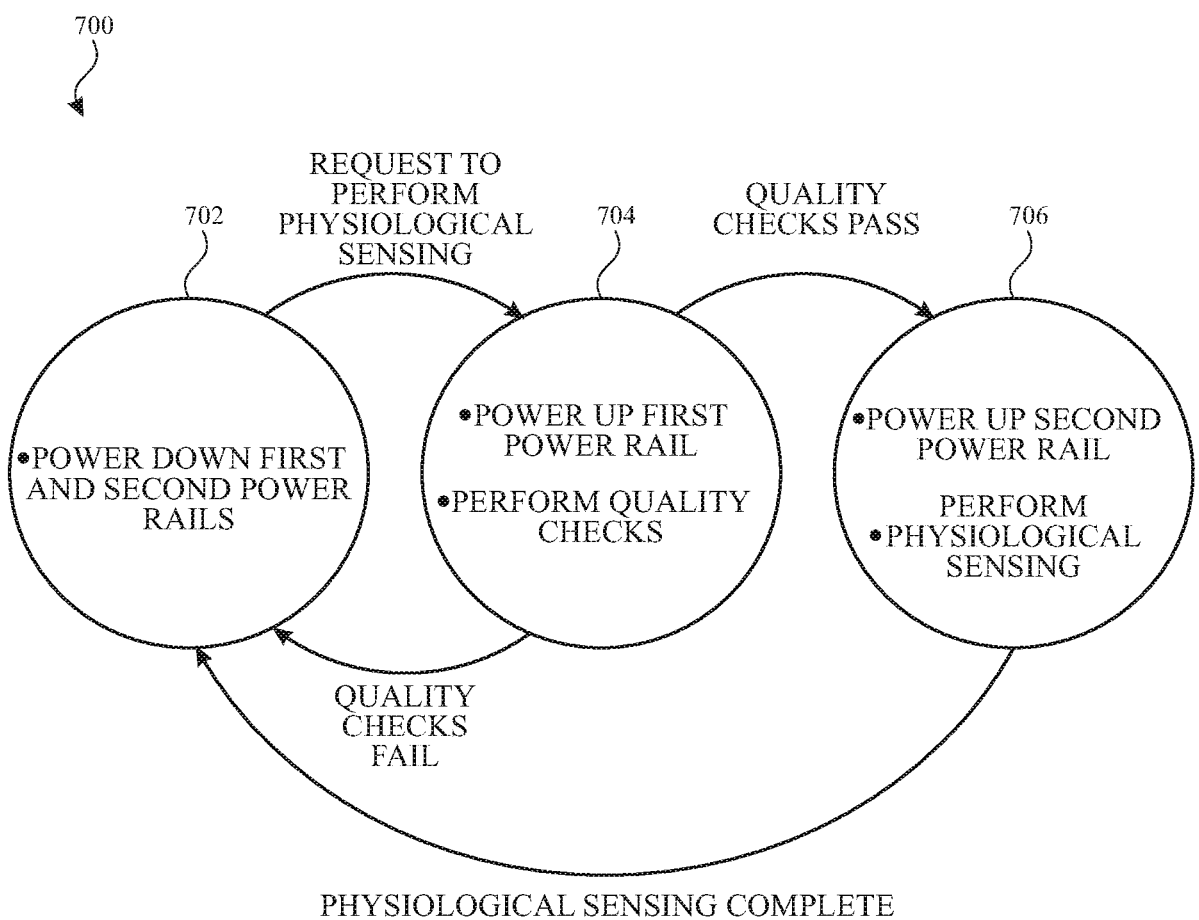
FIG. 7 illustrates an exemplary state diagram according to examples of the disclosure.

FIG. 7 illustrates an exemplary state diagram according to examples of the disclosure. The exemplary state diagram 700 includes three states 702, 704 and 706 indicative of the operation of power rails of a physiological sensing system including a complementary series switch (e.g., corresponding to FIG. 5G). State 702 can correspond to an "idle" state outside of a physiological signal sensing session during which two power rails used for physiological signal sensing can be powered down (and/or remain powered down). State 704 can correspond to a "quality check" state of a physiological signal sensing session during which quality checks can be performed to ensure signal quality for an upcoming physiological signal sensing operation (e.g., checking that the user is properly contacting measurement and reference electrodes to generate a clinically accurate ECG waveform, etc.). During state 704, a first power rail can be powered up (and/or remain powered on) to enable and perform the quality checks. State 706 can correspond to a "sensing" state during which time the physiological sensing operation can be performed (e.g., assuming that signal quality checks pass). During state 706, the first power rail can remain powered up and a second power rail can be powered up (and/or remain powered up).

In some examples, the switching circuit can be operated in the first mode of operation during the quality checks. In some examples, the switching circuit can be operated in the first mode of operation using the first power rail without powering up the second power rail. For example, as illustrated in FIG. 5G, an inverter circuit can be used to generate a complementary gate voltage for the p-mos transistor without powering up a separate power line (e.g., using a negative charge pump). The second power rail can then be turned on as needed for physiological sensing operations during state 706, after quality checks pass. In such a configuration, the power consumption by the physiological signal sensing system can be reduced because the second power rail can be powered down during state 704 without preventing the operation of the switching circuit for quality checks.

Although the disclosure herein primarily focuses on ECG systems and protective circuitry for electrodes of ECG systems, the disclosure can also applicable to other applications including external electrodes that require a low-impedance path in one state (e.g., when the electrode is being sensed) and a high-impedance path and voltage protection when in another state (e.g., when the electrode is not being sensed). It should also be understood that although the switching circuits are primarily described with reference to a ground electrode (and system ground), switching circuitry can be applied for an electrode (e.g., measurement electrode or reference electrode) coupled to a node at a non-ground potential (e.g. a power rail, or other node at a non-ground potential), with the understanding the biasing and control (e.g., rail voltages) of the switching circuitry may be different.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate or ECG may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a device. The device can comprise an external electrode disposed on an external surface of the device, sensing circuitry configured to sense a physiological signal via one or more electrodes (including the external electrode), and a switching circuit coupled between the external electrode and a node at a voltage. The switching circuit can be configured to: in a first mode of operation provide a low-impedance path between the external electrode and the node; and in a second mode of operation provide a high-impedance path between the external electrode and the node. Additionally or alternatively, in some examples, the external electrode can be a ground electrode and the node can be a system ground node. Additionally or alternatively, in some examples, the external electrode can be a reference electrode and the voltage can be different from a system ground voltage. Additionally or alternatively, in some examples, the external electrode can be a measurement electrode and the voltage can be different from a system ground voltage. Additionally or alternatively, in some examples, the switching circuit can comprises a bipolar analog switch. Additionally or alternatively, in some examples, the switching circuit can comprises at least a first transistor and a second transistor coupled in series. Additionally or alternatively, in some examples, the first transistor can be an n-mos transistor and the second transistor can be an n-mos transistor. Additionally or alternatively, in some examples, the first transistor can be a p-mos transistor and the second transistor can be an n-mos transistor. Additionally or alternatively, in some examples, the device can further comprise one or more power rails coupled to the switching circuit. The one or more power rails can be powered on while sensing a physiological signal. Additionally or alternatively, in some examples, the one or more power rails can be powered off while not sensing the physiological signal.

Some examples of the disclosure are directed to a method. The method can comprise: at a device including an external electrode disposed on an external surface of the device and a switching circuit coupled between the external electrode and a node of the device at a voltage: in a first mode of operation, providing a low-impedance path between the external electrode and the node; and in a second mode of operation, providing a high-impedance path between the external electrode and the node. Additionally or alternatively, in some examples, providing the low-impedance path between the external electrode and the node can comprise applying a first gate voltage to a gate of a first transistor to turn on a channel through the first transistor and applying a second gate voltage to a gate of a second transistor to turn on a channel through the second transistor. Additionally or alternatively, in some examples, providing the high-impedance path between the external electrode and the node can comprise grounding the gate of the first transistor to turn off the channel through the first transistor and grounding the gate of the second transistor to turn off the channel through the second transistor. Additionally or alternatively, in some examples, the external electrode can be a ground electrode and the node can be a system ground node. Additionally or alternatively, in some examples, the switching circuit can comprise a p-mos transistor and an n-mos transistor coupled in series. A drain of the p-mos transistor can be coupled to the external electrode, a source of the p-mos transistor can be coupled to a drain of the n-mos transistor, and a source of the n-mos transistor can be coupled to a system ground. Some examples of the disclosure are directed to a non-transitory computer readable storage medium. The non-transitory computer readable storage medium can store instructions, which when executed by one or more processing circuits of a device including an external electrode disposed on an external surface of the device and a switching circuit coupled between the external electrode and a node of the device at a voltage, can cause the one or more processing circuits to perform any of the above methods.

Some examples of the disclosure are directed to a method. The method can comprise: at a device including an external electrode disposed on an external surface of the device and a switching circuit coupled between the external electrode and a node of the device at a voltage: in response to a request to perform physiological sensing, powering up a first power rail of the device coupled to the switching circuit and performing one or more signal quality checks; in accordance with the one or more signal quality checks passing, powering up a second power rail, different from the first power rail, and sensing a physiological signal; and in accordance with the one or more signal quality checks failing, forgo powering up the second power rail and forgo sensing the physiological signal. Additionally or alternatively, in some examples, the method can further comprise: in response to completing the physiological sensing, powering down the first power rail and the second power rail. Additionally or alternatively, in some examples, the external electrode can be a ground electrode and the node can be a system ground node. Additionally or alternatively, in some examples, the switching circuit can comprises a p-mos transistor and an n-mos transistor coupled in series. A gate of the n-mos transistor can be coupled to the first power rail and a gate of the p-mos transistor can be coupled to the first power rail via an inverter circuit. Some examples of the disclosure are directed to a non-transitory computer readable storage medium. The non-transitory computer readable storage medium can store instructions, which when executed by one or more processing circuits of a device including an external electrode disposed on an external surface of the device and a switching circuit coupled between the external electrode and a node of the device at a voltage, can cause the one or more processing circuits to perform any of the above methods. Some examples of the disclosure are directed to a device including an external electrode disposed on an external surface of the device, a switching circuit coupled between the external electrode and a node of the device at a voltage, and processing circuitry programmed to (e.g., configured to) perform any of the above methods.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A device comprising:
   an external electrode disposed on an external surface of the device;
   sensing circuitry configured to sense a physiological signal via one or more electrodes including the external electrode during a first mode of operation;
   a switching circuit coupled between the external electrode and a node at a voltage, the switching circuit configured to:
     in the first mode of operation, provide a low-impedance path between the external electrode and the node; and
     in a second mode of operation different from the first mode of operation, provide a high-impedance path between the external electrode and the node; wherein:
       the external electrode is a ground electrode and the node is a system ground node;
       the external electrode is a reference electrode and the voltage is different from a system ground voltage, or
       the external electrode is a measurement electrode and the voltage is different from the system ground voltage.

2. The device of claim 1, wherein the switching circuit comprises a bipolar analog switch.

3. The device of claim 1, wherein the switching circuit comprises at least a first transistor and a second transistor coupled in series.

4. The device of claim 3, wherein the first transistor is an n-mos transistor and the second transistor is an n-mos transistor.

5. The device of claim 3, wherein the first transistor is a p-mos transistor and the second transistor is an n-mos transistor.

6. The device of claim 5, further comprising:
   one or more power rails coupled to the switching circuit, wherein the one or more power rails are powered on while sensing a physiological signal.

7. The device of claim 6, wherein the one or more power rails are powered off while not sensing the physiological signal.

8. The device of claim 1, wherein the second mode of operation is associated with reducing galvanic corrosion of the external electrode.

9. A method comprising:
   at a device including an external electrode disposed on an external surface of the device and a switching circuit coupled between the external electrode and a node of the device at a voltage:
     in a first mode of operation associated with sensing a physiological signal via the external electrode, providing a low-impedance path between the external electrode and the node; and
     in a second mode of operation, providing a high-impedance path between the external electrode and the node by:
       grounding a gate of a first transistor to turn off a channel through the first transistor; and
       grounding a gate of a second transistor to turn off a channel through the second transistor.

10. The method of claim 9, wherein providing the low-impedance path between the external electrode and the node comprises:
    applying a first gate voltage to the gate of the first transistor to turn on the channel through the first transistor; and
    applying a second gate voltage to the gate of the second transistor to turn on the channel through the second transistor.

11. The method of claim 9, wherein the external electrode is a ground electrode and the node is a system ground node.

12. The method of claim 9, wherein the switching circuit comprises the first transistor and the second transistor coupled in series, wherein the first transistor comprises a first n-mos transistor and the second transistor comprises a second n-mos transistor, wherein a drain of the first n-mos transistor is coupled to the external electrode, a source of the first n-mos transistor is coupled to a source of the second n-mos transistor, and a drain of the second n-mos transistor is coupled to a system ground.

13. A non-transitory computer readable storage medium storing instructions, which when executed by one or more processing circuits of a device including an external electrode disposed on an external surface of the device and a switching circuit coupled between the external electrode and a node of the device at a voltage, cause the one or more processing circuits to perform a method, the method comprising:
- in a first mode of operation associated with sensing a physiological signal via the external electrode, providing a low-impedance path between the external electrode and the node by:
  - applying a first gate voltage to a gate of a first transistor to turn on a channel through the first transistor; and
  - applying a second gate voltage to a gate of a second transistor to turn on a channel through the second transistor; and
- in a second mode of operation different from the first mode of operation, providing a high-impedance path between the external electrode and the node.

14. The non-transitory computer readable storage medium of claim 13, wherein providing the high-impedance path between the external electrode and the node comprises:
- grounding the gate of the first transistor to turn off the channel through the first transistor; and
- grounding the gate of the second transistor to turn off the channel through the second transistor.

15. The non-transitory computer readable storage medium of claim 13, wherein the external electrode is a ground electrode and the node is a system ground node.

16. The non-transitory computer readable storage medium of claim 13, wherein the switching circuit comprises the first transistor and the second transistor coupled in series, wherein the first transistor comprises a first n-mos transistor and the second transistor comprises a second n-mos transistor, wherein a drain of the first n-mos transistor is coupled to the external electrode, a source of the first n-mos transistor is coupled to a source of the second n-mos transistor, and a drain of the second n-mos transistor is coupled to a system ground.

17. A method comprising:
- at a device including an external electrode disposed on an external surface of the device and a switching circuit coupled between the external electrode and a node of the device at a voltage:
  - in response to a request to perform physiological sensing, powering up a first power rail of the device coupled to the switching circuit and performing one or more signal quality checks;
  - in accordance with the one or more signal quality checks passing, powering up a second power rail of the device coupled to the switching circuit, different from the first power rail, and sensing a physiological signal; and
  - in accordance with the one or more signal quality checks failing, forgo powering up the second power rail and forgo sensing the physiological signal.

* * * * *

UNITED STATES PATENT AND TRADEMARK OFFICE
CERTIFICATE OF CORRECTION

| | | |
|---|---|---|
| PATENT NO. | : 11,751,790 B1 | Page 1 of 1 |
| APPLICATION NO. | : 16/551704 | |
| DATED | : September 12, 2023 | |
| INVENTOR(S) | : Priyank Dineshbhai Patel et al. | |

It is certified that error appears in the above-identified patent and that said Letters Patent is hereby corrected as shown below:

In the Claims

In Column 16, Line 19, in Claim 1, delete "voltage," and insert -- voltage; --.

In Column 16, Line 53, in Claim 9, delete "by." and insert -- by: --.

Signed and Sealed this
Sixteenth Day of September, 2025

Coke Morgan Stewart
*Acting Director of the United States Patent and Trademark Office*